United States Patent [19]

Hickmann et al.

[11] 4,429,130
[45] Jan. 31, 1984

[54] PYRID-2'-YL-2-TRIFLUOROMETHYL QUINOL-4-YLMETHANES

[75] Inventors: Eckhard Hickmann, Dannstadt-Schauernheim; Heinz-Guenter Oeser, Dirmstein, both of Fed. Rep. of Germany

[73] Assignee: BASF Aktiengesellschaft, Fed. Rep. of Germany

[21] Appl. No.: 305,858

[22] Filed: Sep. 25, 1981

[30] Foreign Application Priority Data

Oct. 11, 1980 [DE] Fed. Rep. of Germany ..... 30385047

[51] Int. Cl.$^3$ ............................................. C07D 401/06
[52] U.S. Cl. ................................................. 546/167
[58] Field of Search ......................................... 546/176

[56] References Cited

U.S. PATENT DOCUMENTS 2,568,778 9/1951 Surrey et al. ...................... 546/176
2,570,286 10/1951 Surrey et al. ...................... 546/176

FOREIGN PATENT DOCUMENTS 1594282 7/1981 United Kingdom ................ 546/176

OTHER PUBLICATIONS

Takahashi Ann. Rept Itsuu Lao., No. 13, 1963, pp. 25-26.
Antimicrobial Agents and Chemother. 9, 384 (1976).
J. Med. Chem. 14, 926 (1971).
Journal of Labelled Compounds and Radiopharmaceuticals, vol. 17, No. 3 (1980), pp. 431-437.

*Primary Examiner*—Paul M. Coughlan, Jr.
*Assistant Examiner*—D. B. Springer
*Attorney, Agent, or Firm*—Keil & Witherspoon

[57] ABSTRACT

Quinol-4-ylmethane derivatives of the formula I

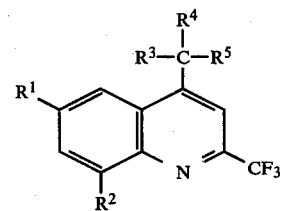

where $R^1$ is hydrogen or chlorine, $R^2$ is trifluoromethyl or chlorine, $R^3$ is a nitrogen-containing, cyclic-unsaturated or acyclic-saturated radical of not more than 6 carbon atoms, $R^4$ is hydrogen or an anion-stabilizing group and $R^5$ is hydrogen, an anion center or an acetal radical of not more than 8 carbon atoms, their preparation and their use for the preparation of quinol-4-ylmethane derivatives.

3 Claims, No Drawings

PYRID-2'-YL-2-TRIFLUOROMETHYL QUINOL-4-YLMETHANES

The present invention relates to novel quinol-4-ylmethane derivatives, their preparation and their use for the preparation of quinol-4-ylmethanol derivatives, which act as drugs, especially against malaria.

Certain quinol-4-ylmethanol derivatives, for example mefloquin (d,l-erythro-(piperid-2'-yl)-2,8-bis-(trifluoromethyl)-quinol-4-ylmethanol, cf., for example, Antimicrobial Agents Chemother. 9 (1976), 384) are valuable active compounds for malaria control. These substances have hitherto been prepared via organometallic intermediates (cf. J.Med.Chem. 14 (1971), 926 and German Laid-Open Application DOS 2,806,909), which has numerous disadvantages for the preparation of relatively large quantities.

We have found that the novel quinol-4-ylmethane derivatives of the formula I

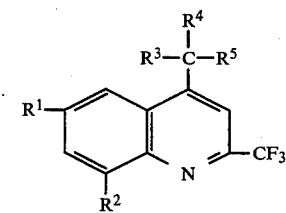

where $R^1$ is hydrogen or chlorine, $R^2$ is trifluoromethyl or chlorine, $R^3$ is a nitrogen-containing, cyclic-unsaturated or acyclic-saturated radical of up to 6 carbon atoms, $R^4$ is hydrogen or an anion-stabilizing group and $R^5$ is hydrogen, an anion center or an acetal radical of not more than 8 carbon atoms, can be prepared in a very simple manner and are valuable intermediates for the preparation of quinol-4-ylmethanol derivatives.

The quinol-4-ylmethane derivatives, according to the invention, of the formula I are prepared by a process in which a compound of the formula II

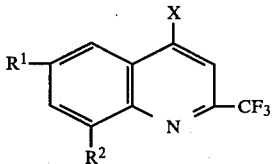

where $R^1$ and $R^2$ have the above meanings and X is an electrofugic group, is reacted with a compound of the formula III

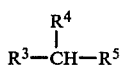

where $R^3$, $R^4$ and $R^5$ have the above meanings, in an inert solvent in the presence of a base.

Particularly suitable electrofugic groups X in formula II are chlorine, bromine and iodine.

The reaction of the compound II with the compound III is carried out in organic solvents which are inert under the reaction conditions, such as aromatic hydrocarbons, eg. benzene, toluene and xylenes, saturated aliphatic and cyclic ethers, eg. diethyl ether, diisopropyl ether, dimethoxyethane, diethylene glycol dimethyl ether, methyl tert.-butyl ether, tetrahydrofuran and dioxane, alcohols, eg. methanol and tert.-butanol, and tertiary amines and trialkylamines, eg. pyridine and triethylamine, as well as aprotic, highly polar solvents, especially acetonitrile, dimethylformamide and dimethylsulfoxide.

In many cases, the reaction can advantageously be carried out in a two-phase system using a phase transfer catalyst. The organic phase is formed by one of the above solvents, whilst the aqueous phase is advantageously an aqueous solution of sodium hydroxide or potassium hydroxide or of sodium carbonate or potassium carbonate. The phase transfer catalyst is one of the quaternary ammonium or phosphonium salts usually employed, such as triethyl-benzyl-ammonium chloride, hexadecyl-trimethylammonium chloride, tricaprylmethyl-ammonium chloride or bromide or hexadecyltributyl-phosphonium bromide.

The reaction of II with III is carried out under base catalysis, for example using alkali metal hydroxides or carbonates or alkaline earth metal hydroxides or carbonates, such as sodium hydroxide, potassium hydroxide or calcium hydroxide or sodium carbonate or potassium carbonate, alkali metal alcoholates, especially the methylate, ethylate, isopropylate or tert.-butylate of sodium or potassium, alkali metal amides, such as sodium amide or potassium amide, or sodium hydride.

The basicity of the base used advantageously matches the acidity of the CH-acidic, nucleophilic component III. Thus, for example, if pyrid-2-yl-acetonitrile is used, aqueous sodium hydroxide solution or an alcoholic alcoholate solution can advantageously be employed, whilst if 2-picoline N-oxide is used as the CH-acidic compound, the reaction is advantageously carried out with a stronger base, such as sodium amide.

The molar ratio of CH-acidic compound III to compound II is usually close to or exactly 1:1. In some cases, for example if III is 2-picoline N-oxide, the molar ratio of III to II is advantageously higher, preferably 2–4:1.

The molar ratio of base to CH-acidic compound III is preferably 2:1.

The reactions are usually carried out at from about −20° C. to the boiling point of the particular solvent, preferably at from about 20° C. to about 60° C., and advantageously under an inert gas atmosphere. Nitrogen and argon are particularly useful inert gases.

The novel compounds are particularly useful for the preparation of quinol-4-ylmethanol derivatives, which are effective against malaria. These derivatives can be obtained in excellent yields and as very pure substances from the novel compounds. Moreover, the novel compounds open up considerably simpler and more reliable routes for the preparation of the quinol-4-yl-methanol derivatives than those which are disclosed, for example, in J.Med.Chem. 14 (1971), 926, German Laid-Open Application DOS 2,806,909 and German Laid-Open Application DOS 2,940,443 and for which organometallic reagents or Grignard compounds are required.

The novel compounds usually do not have to be specially purified for the further reactions. The reaction mixture containing the compound can frequently be further processed directly.

As the Examples show, the desired quinol-4-ylmethanol derivatives can be obtained in excellent yields and as very pure substances from the quinol-4-ylmethane derivatives according to the invention. Thus, (N-oxy)-pyrid-2'-yl-2,8-bis-(trifluoromethyl)-quinol-4- ylmethane can be heated with a carboxylic acid anhydride, eg. acetic anhydride, to give an ester, in this case the acetate, of pyrid-2'-yl-2,8-bis-(trifluoromethyl)-quinol-4-ylmethanol, which gives mefloquin after solvolysis in a solvent containing alcohol and/or water and subsequent or simultaneous hydrogenation.

Pyrid-2'-yl-2,8-bis-(trifluoromethyl)-quinol-4-yl-nitromethane can be converted to pyrid-2'-yl 2,8-bis-(trifluoromethyl)-quinol-4-yl ketone (hereafter referred to as pyridyl ketone) under the conditions of a Nef reaction.

Pyrid-2'-yl-2,8-bis-(trifluoromethyl)-quinol-4-yl-cyanomethane cannot be oxidatively decyanated in a two-phase system by a method similar to that in the literature (Y. Masuyama et al., Chem Letters (1977), 1439), since 2,8-bis-(trifluoromethyl)-quinoline is formed instead of the expected pyridyl ketone. Surprisingly, however, we have found that degradation to give pyridyl ketone can be effected with almost quantitative yields if the reaction is carried out in a polar anhydrous medium, for example an aliphatic alcohol, preferably methanol or tert.-butanol, dimethylformamide, dimethylsulfoxide, hexamethylphosphoric acid triamide or pyridine, in the presence of a base, for example an alcoholate, preferably sodium methylate or potassium tert.-butylate, a tertiary amine, eg. triethylamine or diaza-bicyclo-[2.2.2]-octane, or an inorganic base, eg. calcium hydroxide or potassium carbonate, at room temperature or elevated temperature, whilst gassing with oxygen or oxygen-containing gases, preferably air. A particularly preferred embodiment comprises producing pyrid-2'-yl-2,8-bis-(trifluoromethyl)-quinol-4-yl-cyanomethane from 2,8-bis-(trifluoromethyl)-4-chloro-quinoline and pyrid-2'-ylnitrile in tert.-butanol, as the solvent, in the presence of potassium tert.-butylate as the base, under an inert gas atmosphere, and converting the product, without isolating it, to pyridyl ketone by intensive gassing with air above about 35° C. Pyrid-2'-yl-2,8-bis-(trifluoromethyl)-quinol-4-yl-cyanomethane can also be surprisingly easily converted to pyridyl ketone with oxidizing agents, eg. hydrogen peroxide or peracetic acid, in an acid medium, for example in acetic acid.

Removal of the acetal radical from pyrid-2'-yl-2,8-bis-(trifluoromethyl)-quinol-4-yl-($\alpha$-ethoxy)-ethoxymethane and similar cyanohydrin acetals under acid catalysis and treatment of the resulting cyanohydrin with alkali gives pyridyl ketone.

Pyrid-2'-yl-2,8-bis-(trifluoromethyl)-quinol-4-yl-methino-triphenylphosphate, which is in the form of a ylide, is converted to pyridyl ketone by treatment with oxygen-containing oxidizing agents, triphenylphosphine oxide being split off.

Pyrid-2'-yl-2,8-bis-(trifluoromethyl)-quinol-4-yl-carbethoxymethane can be degraded to pyridyl ketone by saponification and oxidative hydroxylation.

Pyrid-2'-yl-2-trifluoromethyl-6,8-dichloro-quinol-4-yl-cyanomethane can be converted to pyrid-2'-yl 6,8-dichloro-quinol-4-yl ketone by a method similar to that used on pyrid-2'-yl-2,8-bis-(trifluoromethyl)-quinol-4-yl-cyanomethane. The catalytic hydrogenation of the product gives the desired (piperid-2'-yl)-2-trifluoromethyl-6,8-dichloro-quinol-4-ylmethanol.

(N-Oxy)-pyrid-2'-yl-2-trifluoromethyl-6,8-dichloroquinol-4-ylmethane can be converted to (piperid-2'-yl)-2-trifluoromethyl-6,8-dichloro-quinol-4-ylmethanol by a method similar to that used on (N-oxy)-pyrid-2'-yl-2,8-bis-(trifluoromethyl)-quinol-4-ylmethane.

The Examples which follow illustrate the invention in more detail. In these Examples, parts by volume bear the same relation to parts as that of the liter to the kilogram.

I. PREPARATION OF THE NOVEL COMPOUNDS

EXAMPLE 1

11.0 parts of 2-picoline N-oxide are added to a suspension of 4.75 parts of sodium amide in 150 parts by volume of dimethoxyethane. 10.3 parts of 2,8-bis-(trifluoromethyl)-4-bromoquinoline are then added at from 20° to 27° C. and the mixture is stirred at room temperature for half an hour, acidified with 10 parts of glacial acetic acid and evaporated to dryness. Extraction of the evaporation residue with toluene gives 9.2 parts=83% of theory of (N-oxy)-pyrid-2'-yl-2,8-bis-(trifluoromethyl)-quinol-4-ylmethane. The mass spectrum of the compound indicates that it is almost pure, with a molecular peak at 372.

EXAMPLE 2

20 parts by volume of concentrated sodium hydroxide solution are added to a mixture of 13.8 parts of pyrid-2-yl-nitromethane, 34.4 parts of 2,8-bis-(trifluoromethyl)-4-bromoquinoline, 0.5 part of tetrabutylammonium chloride and 100 parts by volume of dimethylsulfoxide at room temperature under nitrogen, with stirring; during this addition, the temperature rises to 39° C. After the mixture has been stirred at about 40° C. for three hours, the starting substances can no longer be detected by thin layer chromatography. The mixture is diluted with 300 parts by volume of water and acidified to pH 3 with concentrated hydrochloric acid, and the product is extracted five times, with 50 parts by volume of methylene chloride each time. The combined extracts are washed twice with 50 parts by volume of water each time and concentrated. 35.8 parts=89.3% of theory of pyrid-2'-yl-2,8-bis-(trifluoromethyl)-quinol-4-yl-nitromethane of melting point 182°–183° C. are obtained. The mass spectrum of the substance shows a molecular peak at 401.

EXAMPLE 3

35.5 parts of concentrated sodium hydroxide solution are added to a mixture of 62 parts of 2,8-bis-(trifluoromethyl)-4-bromoquinoline, 106 parts by volume of dimethylformamide (DMF), 1.7 parts of tetrabutylammonium chloride and 20.9 parts of pyrid-2-yl-acetonitrile at room temperature, whilst gassing with nitrogen, and the reaction mixture is stirred for one hour. About 200 parts by volume of water are then added and the mixture is adjusted to pH 4 with glacial acetic acid. The product which has precipitated is filtered off with suction, washed thoroughly with water and dried. 67 parts=97.6% of theory of pyrid-2'-yl-2,8-bis-(trifluoromethyl)-quinol-4-yl-cyanomethane of melting point 162°–165° C. are obtained. An analytically pure sample has a melting point of 167°–168° C.

EXAMPLE 4

(a) Preparation of the starting material

A mixture of 100 parts by volume of phosphorus trichloride and 40 parts of 2,8-bis-(trifluoromethyl)-4-hydroxyquinoline is refluxed for 8 hours. Most of the excess phosphorus trichloride is then distilled off, the residue is poured onto 200 parts of ice-water and the pH is brought to 12–13 with 12 N sodium hydroxide solution. The mixture is then extracted with methylene chloride, the extract is dried over sodium sulfate and the solvent is stripped off under reduced pressure. 40.2 parts = 94% of theory of 2,8-bis-(trifluoromethyl)-4-chloroquinoline of melting point 40°–42° C. are obtained.

(b) Preparation of the quinol-4-ylmethane derivative 63.5 parts = 88% of theory of pyrid-2'-yl-2,8-bis-(trifluoromethyl)-quinol-4-yl-cyanomethane of melting point 162°–164° C. are obtained by a method similar to that in Example 3, using 54 parts of the product obtained as described in 4a).

EXAMPLE 5

23.6 parts of pyrid-2-yl-acetonitrile are added to a mixture of 250 parts by volume of tert.-butanol, 44.9 parts of potassium tert.-butylate and 57.1 parts of 2,8-bis-(trifluoromethyl)-4-chloroquinoline at room temperature, with stirring, and the mixture is stirred under nitrogen for about 1.5 hours. 12.0 parts of acetic acid are added and the mixture is diluted with about 300 parts by volume of water. The product which has precipitated is washed thoroughly with water and dried at about 50° C. in an oven under reduced pressure. 74.3 parts = 97.5% of theory of pyrid-2'-yl-2,8-bis-(trifluoromethyl)-quinol-4-yl-cyanomethane (cf. Example 3) of melting point 163°–165° C. are obtained.

EXAMPLE 6

A mixture of 200 parts by volume of DMF, 17.2 parts of 2,8-bis-(trifluoromethyl)-4-bromoquinoline, 30.4 parts of finely powdered potassium carbonate and 9.0 parts of 2-picolyl chloride hydrochloride is stirred at room temperature under nitrogen for 2 hours. 5.4 parts of potassium cyanide are then added a little at a time and the mixture is heated to 50° C. and stirred for a further 16 hours. Undissolved material is filtered off and the filtrate is neutralized with 3 parts of glacial acetic acid and diluted with 300 ml of water. The product which has precipitated is filtered off with suction, washed with water and dried in an oven under reduced pressure at about 50° C. 18 parts = 95% of theory of crude pyrid-2'-yl-2,8-bis-(trifluoromethyl)-quinol-4-yl-cyanomethane (cf. Example 3), containing a little pyrid-2'-yl-2-picolyl-2,8-bis-(trifluoromethyl)-quinol-4-yl-cyanomethane as a by-product, are obtained.

EXAMPLE 7

13.5 parts of potassium tert.-butylate are added to a mixture of 250 parts by volume of tert.-butanol, 20.6 parts of 2,8-bis-(trifluoromethyl)-4-bromoquinoline and 7.1 parts of pyrid-2-yl-acetonitrile under nitrogen, and the mixture is stirred at room temperature for about 1.5 hours. The resulting reaction mixture contains pyrid-2'-yl-2,8-bis-(trifluoromethyl)-quinol-4-yl-cyanomethane (cf. Example 3) in the form of its intensely permanganate-colored potassium salt. The mixture can be further used directly (cf. Example H).

EXAMPLE 8

(a) Preparation of the starting material

A mixture of 190 parts by volume of methylene chloride, 17 parts of crude pyridin-2-aldehyde cyanohydrin, 10 parts of vinyl ethyl ether and 0.3 part of p-toluenesulfonic acid is stirred at 40° C. for 1.5 hours. 5 parts of powdered potassium carbonate are then added, the mixture is stirred for a further hour, the organic phase is filtered and washed with water and the organic solvent is stripped off. The residue is partitioned between 100 parts by volume of toluene and 10 parts by volume of 2 N sodium hydroxide solution, the organic phase is evaporated and the residue (5.3 parts) is distilled under reduced pressure. 3.3 parts of pyrid-2-yl-($\alpha$-ethoxy)-ethoxyacetonitrile of boiling point$_{0.3}$ 80°–85° C. are obtained.

(b) Preparation of the quinol-4-ylmethane derivative

A mixture of 10 parts of concentrated sodium hydroxide solution and 20 parts of water is slowly added to a mixture of 10.6 parts of pyrid-2-yl-($\alpha$-ethoxy)-ethoxy-acetonitrile, 17.3 parts of 2,8-bis-(trifluoromethyl)-4-bromoquinoline, 0.5 part of tetrabutylammonium chloride and 50 parts by volume of dimethylsulfoxide at room temperature under nitrogen, with stirring; during this addition, the temperature rises to about 28° C. After a reaction period of half an hour, the starting substances can no longer be detected by thin layer chromatography. The mixture is diluted with 200 parts of water and the product is extracted three times with 50 parts by volume of toluene each time. The combined toluene extracts are washed once with 100 parts of water and evaporated. 19.5 parts = 82.5% of theory of pyrid-2'-yl-2,8-bis-(trifluoromethyl)-quinol-4-yl-($\alpha$-ethoxy)-ethoxy-methane are obtained as an oil with the appropriate mass spectrum (molecular peak at 469).

EXAMPLE 9

(a) Preparation of the starting material

A mixture of 60 parts by volume of DMF, 6.4 parts of 2-picolyl chloride and 13.2 parts of triphenylphosphine is stirred at 100° C. under nitrogen for 4 hours. The crystals which have precipitated are filtered off with suction, washed with petroleum ether and dried. 12 parts = 59% of theory of triphenyl-2-picolylphosphonium chloride are obtained.

(b) Preparation of the quinol-4-ylmethane derivative

A mixture of 50 parts by volume of DMF, 34.4 parts of 2,8-bis-(trifluoromethyl)-4-bromoquinoline, 40.4 parts of triphenyl-2-picolyl-phosphonium chloride and 110 parts of potassium carbonate is stirred under nitrogen for 3 hours, the mixture finally being heated to 155° C. The reaction mixture is diluted with about 200 parts by volume of water and is extracted twice, with 100 parts by volume of toluene each time. The toluene extract is evaporated and the residue is reprecipitated from toluene/hexane. 56 parts = 89% of theory of pyrid-2'-yl-2,8-bis-(trifluoromethyl)-quinol-4-yl-methinotriphenylphosphane of melting point 153°–155° C. are obtained. In the NMR spectrum, the product has a singlet at $\delta = 7.28$ ppm (proton in the 3-position of the quinoline ring). The mass spectrum shows a molecular peak at 627.

EXAMPLE 10

A mixture of 1,000 parts by volume of DMF, 86 parts of 2,8-bis-(trifluoromethyl)-4-bromoquinoline, 41 parts of ethyl pyrid-2-yl-acetate and 138 parts of potassium carbonate is heated at 100° C. for 2 hours, with stirring. Undissolved material is then filtered off, 15 parts of glacial acetic acid are added to the filtrate and the mixture is diluted with 2,000 parts by volume of water and extracted twice, with 1,000 parts by volume of toluene each time. The combined toluene extracts are evaporated and the resulting residue is digested with petroleum ether, filtered off with suction and dried. 102 parts=92% of theory of pyrid-2'-yl-2,8-bis-(trifluoromethyl)-quinol-4-yl-carbethoxymethane of melting point 95°–96° C. are obtained. The NMR spectrum of this compound shows, inter alia, the typical bands for the ethyl group and a singlet at $\delta=6.57$ ppm (proton of the methine group) and at $\delta=8.02$ (proton in the 3-position of the quinoline ring).

EXAMPLE 11

One part of tetrabutylammonium chloride is added to a mixture of 800 parts of volume of DMF, 85.6 parts of pyrid-2-yl-acetonitrile and 250 parts of 2-trifluoromethyl-6,8-dichloro-4-bromoquinoline, 150 parts of concentrated sodium chloride solution are added at room temperature, with cooling, and the mixture is stirred under nitrogen for 1.5 hours. The DMF phase is separated off, mixed with 45 parts of glacial acetic acid and diluted with 1,000 parts by volume of water. The product which has precipitated is filtered off with suction, washed with water and dried at about 50° C. in an oven under reduced pressure. 255 parts=92% of theory of pyrid-2'-yl-2-trifluoromethyl-6,8-dichloro-quinol-4-yl-cyanomethane of melting point 171°–173° C. are obtained.

EXAMPLE 12

(a) Preparation of the starting material

A procedure similar to that described in Example 4a) is followed, using 40 parts of 2-trifluoromethyl-6,8-dichloro-4-hydroxyquinoline instead of 2,8-bis-(trifluoromethyl)-4-hydroxyquinoline. 38.9 parts=91% of theory of 2-trifluoromethyl-4,6,8-trichloroquinoline of melting point 74°–76° C. are thus obtained.

(b) Preparation of the quinol-4-ylmethane derivative

The procedure followed is as described in Example 5, using 57.3 parts of 2-trifluoromethyl-4,6,8-trichloroquinoline instead of 2,8-bis-(trifluoromethyl)-4-chloroquinoline. 69.5 parts=95% of theory of pyrid-2'-yl-2-trifluoromethyl-6,8-dichloro-quinol-4-yl-cyanomethane of melting point 172°–173° C. are thus obtained.

EXAMPLE 13

A solution of 22 parts of 2-trifluoromethyl-4,6,8-trichloroquinoline in 70 parts by volume of toluene is added dropwise to a solution, which has been cooled to $-35°$ C., of 9.5 parts of sodium amide in about 600 parts by volume of liquid ammonia in the course of about 30 minutes, with stirring. 500 parts by volume of toluene are then slowly added, during which addition the ammonia evaporates. The orange suspension is left to come to room temperature, whilst gassing with nitrogen, a solution of 18.0 parts of 2-trifluoromethyl-4,6,8-trichloroquinoline in 60 parts by volume of toluene is added, the mixture is stirred for 10 hours, 300 parts by volume of water are added, and the organic phase is separated off and evaporated. The resulting crude product (31.5 parts) is boiled up twice, with about 300 ml of n-hexane each time, the combined extracts are evaporated and the residue is recrystallized from methanol. 21.1 parts=77% of theory of (N-oxy)-pyrid-2'-yl-2-trifluoromethyl-6,8-dichloro-quinol-4-ylmethane of melting point 195°–197° C. are obtained.

II. USE OF THE NEW COMPOUNDS

EXAMPLE A (a) A solution of 20 parts of (N-oxy)-pyrid-2'-yl-2,8-bis-(trifluoromethyl)-quinol-4-ylmethane (Example 1) in 100 parts by volume of acetic anhydride is heated at 70° C. for one hour. The reaction mixture is evaporated and the evaporation residue is boiled up with toluene to give 18 parts=84% of theory of pyrid-2'-yl-2,8-bis-(trifluoromethyl)-quinol-4-yl-acetoxymethane of melting point 104°–106° C.

(b) A mixture of 41.4 parts of pyrid-2'-yl-2,8-bis-(trifluoromethyl)-quinol-4-yl-acetoxymethane, 1,000 parts by volume of 95% strength ethanol, 15 parts of concentrated hydrochloric acid and 10 parts of a hydrogenation catalyst (5% platinum-on-graphite; supplier: Heraeus) is heated at the boiling point under nitrogen for 2 hours. It is cooled to room temperature, the nitrogen is replaced by hydrogen, and hydrogenation is carried out at 28° C. and under atmospheric pressure, with thorough stirring, until 7,500 parts by volume of hydrogen have been taken up. The hydrogenation catalyst is then filtered off and the solution is evaporated. 41.2 parts=99.4% of theory of hydrogenation product containing about 85% of mefloquin hydrochloride (cf. the introduction to the description, paragraph 2) are obtained.

EXAMPLE B

Oxygen is passed into a solution of 40 parts of pyrid-2'-yl-2,8-bis-(trifluoromethyl)-quinol-4-yl-cyanomethane (Example 5) and 12.6 parts of potassium tert.-butylate in 200 parts by volume of tert.-butanol at room temperature for 3 hours. About 1,000 parts by volume of water are then added to the reaction mixture and the mixture is extracted three times, with 500 parts by volume of toluene each time. The toluene extract is washed with water and evaporated. 38 parts=97.8% of theory of pyrid-2'-yl 2,8-bis-(trifluoromethyl)-quinol-4-yl ketone of melting point 114°–118° C. are obtained.

EXAMPLE C

Oxygen is passed into a mixture of 4.0 parts of pyrid-2'-yl-2,8-bis-(trifluoromethyl)-quinol-4-yl-cyanomethane (Example 3), 4.7 parts of 30% strength methanolic sodium methylate solution and 10 parts by volume of methanol at 40° C. for 9 hours and for a further 5 hours at 50° C., with stirring. 100 parts by volume of water are added and the mixture is extracted three times, with 100 parts by volume of toluene each time. The combined organic phases are concentrated to dryness. 3.4 parts=88% of theory of pyrid-2'-yl 2,8-bis-(trifluoromethyl)-quinol-4-yl ketone, which is pure according to thin layer chromatography, are obtained.

EXAMPLE D

Oxygen is passed into a mixture of 4.0 parts of pyrid-2'-yl-2,8-bis-(trifluoromethyl)-quinol-4-yl-cyanomethane (Example 3), 1.46 parts of diaza-bicyclo-[2.2.2]octane and 20 parts by volume of dimethylformamide at 50° C. for 10 hours and for a further 2 hours at 60° C., with stirring. After the working up described in Example C, 2.9 parts=64% of theory of pyrid-2'-yl 2,8-bis-(trifluoromethyl)-quinol-4-yl ketone are obtained.

EXAMPLE E

Oxygen is passed into a mixture of 4.0 parts of pyrid-2'-yl-2,8-bis-(trifluoromethyl)-quinol-4-yl-cyanomethane (Example 3), 1,0 part of calcium hydroxide and 20 parts by volume of dimethylformamide at 50° C. for 17 hours, with stirring. After working up as described in Example C, 3.2 parts=82% of theory of pyrid-2'-yl-2,8-bis(trifluoromethyl)-quinol-4-yl ketone are obtained.

EXAMPLE F

A mixture of 250 parts by volume of tert.-butanol, 7.07 parts of potassium tert.-butylate and 22.9 parts of pyrid-2'-yl-2,8-bis-(trifluoromethyl)-quinol-4-yl-cyanomethane (Example 3) is heated at 60° C. Air is passed in at this temperature, with thorough mixing, until the nitrile has reacted. 3.8 parts of glacial acetic acid are added and the mixture is diluted with 300 parts by volume of water. The product which has precipitated is filtered off, washed with water and dried at 50° C. in an oven under reduced pressure. 21.6 parts=97% of theory of pyrid-2'-yl 2,8-bis-(trifluoromethyl)-quinol-4-yl ketone of melting point 128°–129° C. are obtained.

EXAMPLE G

A solution of 5.0 parts of pyrid-2'-yl-2,8-bis-(trifluoromethyl)-quinol-4-yl-cyanomethane in 20 parts by volume of glacial acetic acid is heated to 110° C., and 1.1 parts of 50% strength hydrogen peroxide are added in the course of 5 minutes. The mixture is then stirred at the boiling point for one hour. The excess hydrogen peroxide is destroyed by adding sodium sulfite and, after addition of 50 parts by volume of water, the reaction mixture is extracted twice, with 100 parts by volume of toluene each time. Evaporation of the toluene solution gives 4.1 parts=84% of theory of pyrid-2'-yl 2,8-bis-(trifluoromethyl)-quinol-4-yl ketone.

EXAMPLE H

The mixture obtained according to Example 7 is heated to 50°–60° C. and air is passed through for about 15 hours, with thorough mixing. 3.6 parts of glacial acetic acid are then added and the reaction mixture is diluted with 300 parts by volume of water. The product which has precipitated is washed thoroughly with water and dried at about 50° C. in an oven under reduced pressure. 21.3 parts=96% of theory of pyrid-2'-yl 2,8-bis-(trifluoromethyl)-quinol-4-yl ketone of melting point 127°–128° C. are obtained.

EXAMPLE I

A mixture of 100 parts by volume of methanol, 4.7 parts of pyrid-2'-yl-2,8-bis-(trifluoromethyl)-quinol-4-yl-(α-ethoxy)-ethoxymethane (Example 8) and 1 part of concentrated hydrochloric acid is stirred at room temperature for 3 hours. 5 parts by volume of 6 N sodium hydroxide solution and 200 parts by volume of water are then added, the mixture is stirred for another half hour and the product which was precipitated is filtered off with suction, washed with water and dried. 2.5 parts=68% of theory of pyrid-2'-yl 2,8-bis-(trifluoromethyl)-quinol-4-yl ketone of melting point 113°–116° C. are obtained.

EXAMPLE K

Air is passed into a mixture of 170 parts by volume of tert.-butanol, 11.4 parts of pyrid-2'-yl-2-trifluoromethyl-6,8-dichloro-quinol-4-yl-cyanomethane (Example 12) and 3.5 parts of potassium tert.-butylate at 60° C., with thorough mixing. When the reaction has ended, 3.0 parts of glacial acetic acid are added and the reaction mixture is diluted with 300 parts by volume of water. The product which has precipitated is filtered off with suction, washed with water and dried at 50° C. in an oven under reduced pressure. 10.8 parts=80% of theory of pryid-2'-yl 2-trifluoromethyl-6,8-dichloroquinol-4-yl ketone of melting point 193°–194° C. are obtained.

EXAMPLE L

The procedure followed is as described in Example G, using 5.0 parts of pyrid-2'-yl-2-trifluoromethyl-6,8-dichloro-quinol-4-yl-cyanomethane (Example 12) instead of pyrid-2'-yl-2,8-bis-(trifluoromethyl)-quinol-4-yl-cyanomethane. After the same working up, 4.25 parts=87.5% of theory of pyrid-2'-yl 2-trifluoromethyl-6,8-dichloro-quinol-4-yl ketone are obtained.

EXAMPLE M (a) A mixture of 40 parts of (N-oxy)-pyrid-2'-yl-2-trifluoromethyl-6,8-dichloro-quinol-4-ylmethane (Example 13) and 300 parts by volume of acetic anhydride is heated at 70° C. for one hour. The solvent is distilled off, the resulting crude product (46.1 parts) is boiled up twice, with 400 ml of n-hexane each time and the combined extracts are evaporated and recrystallized from ethyl acetate. 31.8 parts=71% of theory of pyrid-2'-yl-2-trifluoromethyl-6,8-dichloro-quinol-4-yl-acetoxymethane of melting point 143°–145° C. are obtained.

(b) 20.8 parts of the compound thus obtained are hydrogenated at 25° C. by a method similar to that in Example A, (b), until 4,900 parts by volume of hydrogen have been taken up. 20.5 parts=98.6% of theory of (piperid-2'-yl)-2-trifluoromethyl-6,8-dichloro-quinol-4-ylmethanol are obtained as the hydrochloride.

We claim:

1. A compound of the formula I

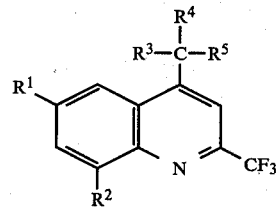

where $R^1$ is hydrogen or chlorine, $R^2$ is trifluoromethyl or chlorine, $R^3$ is 2-pyridyl, $R^4$ is cyano and $R^5$ is hydrogen.

2. A compound of the formula I of claim 1, wherein $R^1$ is hydrogen and $R^2$ is trifluoromethyl.

3. A compound of the formula I of claim 1, wherein $R^1$ is chlorine and $R^2$ is chlorine.

* * * * *